United States Patent [19]

Soejima et al.

[11] Patent Number: 4,581,332

[45] Date of Patent: Apr. 8, 1986

[54] NOVEL ALKALINE PROTEASE

[75] Inventors: Masami Soejima; Takeharu Masaki, both of Ibaraki; Hideya Suzuki, Saitama, all of Japan

[73] Assignee: Wako Pure Chemical Industries, Ltd., Osaka, Japan

[21] Appl. No.: 536,814

[22] Filed: Sep. 28, 1983

[30] Foreign Application Priority Data

Sep. 28, 1982 [JP] Japan .................................. 57-169428

[51] Int. Cl.[4] .......................... C12N 9/52; C12N 9/50; C12R 1/025
[52] U.S. Cl. .................................... 435/220; 435/219; 435/824
[58] Field of Search ........................ 435/212, 219, 220

[56] References Cited

U.S. PATENT DOCUMENTS 4,320,197 3/1982 Morihara et al. ..................... 435/70

OTHER PUBLICATIONS

Agricultural and Biological Chemistry 42 (7) 1443–1445 (1978).
Biochemical Biophysical Research Communications vol. 92 pp. 396–402, (1980).

Primary Examiner—Lionel M. Shapiro
Attorney, Agent, or Firm—Sughrue, Mion, Zinn Macpeak & Seas

[57] ABSTRACT

A novel protease is described. The enzyme has the following characteristics: molecular weight: 30,000 (a gel filtration method using Sephadex G-75); isoelectric point, 5.3; pH reactivity: the optimum pH for its esterase activity is at pH 8.5 and the optimum pH for its amidase activity is at pH 9.0 respectively; substrate reactivity: it selectively and specifically hydrolyzes the ester bond and the amide bond derived from the carboxyl group of L-lysine; inhibitor: it is inhibited by diisopropyl phosphofluoride, tosyl-L-lysine chloromethyl ketone and phenylmethylsulfonyl chloride. The protease is preferably produced by a microorganism belonging to the genus Achromobacter.

10 Claims, 6 Drawing Figures

NOVEL ALKALINE PROTEASE

FIELD OF THE INVENTION

The present invention relates to a novel alkaline protease which has a specificity to lysyl bonds and which is produced by a bacteria, *Achromobacter lyticus*, separated from soil.

BACKGROUND OF THE INVENTION

The bacteria *Achromobacter lyticus* produces a lytic enzyme and an alkaline protease; the lytic enzyme is described in Japanese Patent Publication No. 42953/71 and, the alkaline protease, which was discovered by the present inventors and given the name Achromobacter protease I is described in *Agricultural and Biological Chemistry*, vol. 42, page 1442 (1978).

As a result of further detailed investigations on enzyme systems, particularly protease systems, produced by *Achromobacter lyticus*, the present inventors have found by fractionation of isoelectric point focusing electrophoresis using Ampholite (trademark of LKB Co., Ltd.) having pH 3.5 to 10 that a protease obviously different from protease I is present. The present inventors have further succeeded in isolating a novel protease from the fraction and named the fraction protease Ia (hereafter the novel alkaline protease of the present invention is referred to as protease Ia).

The present inventors have extensively investigated a method for obtaining the enzyme and various properties, as well as a method for utilization of the enzyme.

SUMMARY OF THE INVENTION

One object of the present invention is to describe a new protease.

Another object of the present invention is to describe a new protease produced by a microorganism belonging to the genus Achromobacter.

Accordingly, one embodiment of the present invention is a protease having the characteristics described below:

(i) molecular weight: 30,000 (a gel filtration method using Sephadex G-75)

(ii) Isoelectric point: 5.3

(iii) ph reactivity: it has an optimum pH for esterase activity at pH 8.5 and an optimum pH for amidase activity at pH 9.0 respectively.

(iv) substrate reactivity: it selectively and specifically hydrolyzes the ester bond and the amide bond derived from the carboxyl group of L-lysine.

(v) inhibitor: it is inhibited by diisopropyl phosphofluoride, tosyl-L-lysine chloromethyl ketone and phenylmethylsulfonyl chloride.

The protease of the present invention is preferably produced by a microorganism belonging to the genus Achromobacter.

BRIEF DESCRIPTION OF THE DRAWINGS

FIG. 3 is a graph showing pH stability. In FIG. 3, —O— represents a 0.1M calcium acetate buffer, —.— represents 0.1M tris-HCl buffer, —△— represents 0.1M diol-HCl buffer, and —▲— represents 0.1M disodium phosphate-NaOH buffer.

DETAILED DESCRIPTION OF THE INVENTION

*Achromobacter lyticus* M497-1 has been deposited in Foundation, Institute for Fermentation, Osaka under IFO 12725, American Type Culture Collection under ATCC 21456 and Fermentation Research Institute, Agency of Industrial Science and Technology, Ministry of International Trade and Industry of Japan under FERM-P 4420, respectively.

The production of the enzyme is carried out by cultivating a bacteria producing a novel protease and belonging to the genus Achromobacter in a culture medium. The culture medium may be a solid or a liquid. Cultivation may be in settled culture, but it is generally more advantageous if cultivation is carried out under aerobic conditions in a liquid medium by shaking the culture or by aeration of a spinner culture, etc.

Any material may be added to a culture medium composition as long as the growth of the bacteria and the production of protease Ia are accelerated.

Examples of the carbon source include sugars such as glucose, saccharose, dextrin, etc. Examples of the nitrogen source include organic or inorganic nitrogen-containing compounds such as peptone, meat extract, yeast extract, dry yeast, soybean powders, casein, casamino acids, amino acids, ammonium salts, etc. As inorganic salts, metals such as sodium, potassium, calcium, magnesium, etc., may also be added in the form of phosphates, sulfates, carbonates, chlorides, etc. Vitamins, nucleic acids and compounds related thereto may also be added for accelerating the growth of the bacteria and the production of protease Ia in some cases.

Culture conditions such as pH of medium, culture temperature, amount of aeration, incubation time, etc., vary depending upon the strains used, the composition of medium, etc., and should be chosen and controlled appropriately so that the maximum amount of the desired protease Ia will accumulate. In most cases, the pH of a medium is about neutral, culture temperature is between 20° and 35° C., preferably 25° and 30° C., the aeration amount is from about 0.5 to 1.5 l/min per liter of medium, and incubation time is for about 1 to 2 days.

Thus, a bacteria producing protease Ia is cultured and protease Ia is secreted and accumulated in the culture liquid.

To obtain the enzyme, conventional means for separation and purification can suitably be utilized and will yield a standard material of a desired purity. For example, the product can be fractionally precipitated by salting out through the addition of salts such as ammonium sulfate, etc. to the supernatant or the filtrate obtained after removing bacterial cells by a process such as centrifugal separation or filtration, etc.; or by adding a hydrophilic organic solvent such as alcohols, acetone, etc. to the supernatant or the filtrate. Further, the degree of purification can be enhanced by adsorption and desorption using, e.g., alumina, bentonite, calcium phosphate gel, activated carbon, etc., a chromatographic method using various ion exchange materials, a molecular sieve method using Sephadex, biogel. etc., singly or in suitable combinations thereof. In addition, an isoelectric point precipitation method, a dialysis method, an electrophoresis method, a precipitation method using heavy metal ions, etc., can also be employed to enhance the degree of purification. As above, protease Ia of a desired purity can be separated.

A method for obtaining the enyzme will be explained in more detail with reference to the examples described hereafter. Titers of amidase activity and esterase activity are determined to have units, by the following methods:

METHOD FOR MEASUREMENT OF AMIDASE ACTIVITY AND UNIT

To 1.3 ml of a 0.2M 2-amino-2-methyl-1,3-propanediol buffer solution (pH 9.5), 0.15 ml of a 2.5 mM benzoyl-DL-lysine-p-nitroanilide (hereafter simply referred to as Bz-Lys-p-NA) aqueous solution was added. After preliminarily warming the above solution to 30° C., 0.05 ml of an enzyme solution was added thereto and the mixture was reacted accurately for 25 minutes. After completion of the reaction, 0.5 ml of a 45% (v/v) aqueous acetic acid solution was added to discontinue the reaction. Then, the reaction liquid was colorimetrically measured at 405 nm and its absorbance was determined. As an enzyme unit, an amount of the enzyme that produced 1 µmole of p-nitroaniline per 1 minute at 30° C. was defined as 1 unit (1 u). A method for calculating enzyme titer was in accordance with the following equation:

Activity (u/ml) =

$$\Delta OD/min \times \frac{1}{9.62} \times \frac{2.0}{0.05} \times \text{dilution magnification}$$

METHOD FOR MEASUREMENT OF ESTERASE ACTIVITY AND UNIT

After preliminarily warming 3.0 ml of a 40 mM tris-hydrochloride buffer solution (pH 8.0) containing 1 mM tosyl-L-lysine-methyl ester (hereafter referred to as TLME) at 30° C., 0.2 ml of an enzyme solution was added thereto and the change in absorbance ($\Delta OD$) was measured at 247 nm and 30° C. An amount of the enzyme that hydrolyzed 1 µmole of TLME per 1 minute at 30° C. was defined as 1 unit. A method for calculating an enzyme titer was in accordance with the following equation.

Activity (u/ml) =

$$\Delta OD/min \times \frac{1}{0.96} \times \frac{3.2}{0.2} \times \text{dilution magnification}$$

Enzymatic and chemical characteristics of protease Ia of the present invention will next be described.

(i) molecular weight: 30,000 (a gel filtration method using Sephadex G-75)

(ii) isoelectric point (by an isoelectric fractionation method using Ampholine): pH 5.3.

Figure 1:
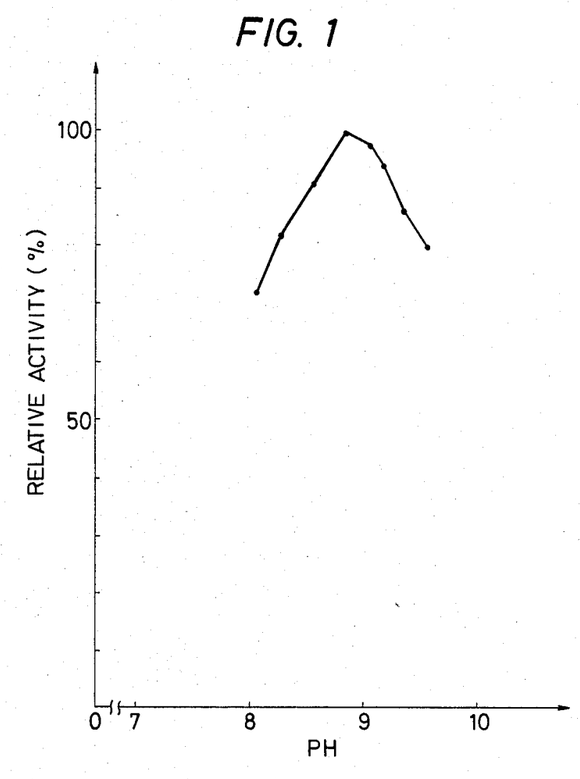
FIG. 1 is a graph showing the relationship between pH and amidase activity.
Figure 2:
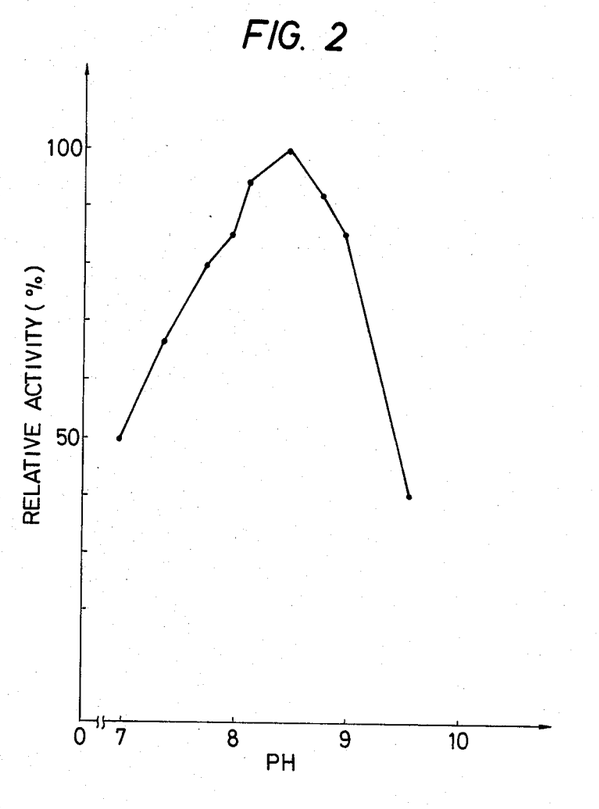
FIG. 2 is a graph showing the relationship between pH and esterase activity.

(iii) pH reactively: the amidase activity is optimal at pH 9.0 for Bz-Lys-p-NA (refer to FIG. 1) and the esterase activity is optimal at pH 8.5 for TLME (refer to FIG. 2).

Figure 3:
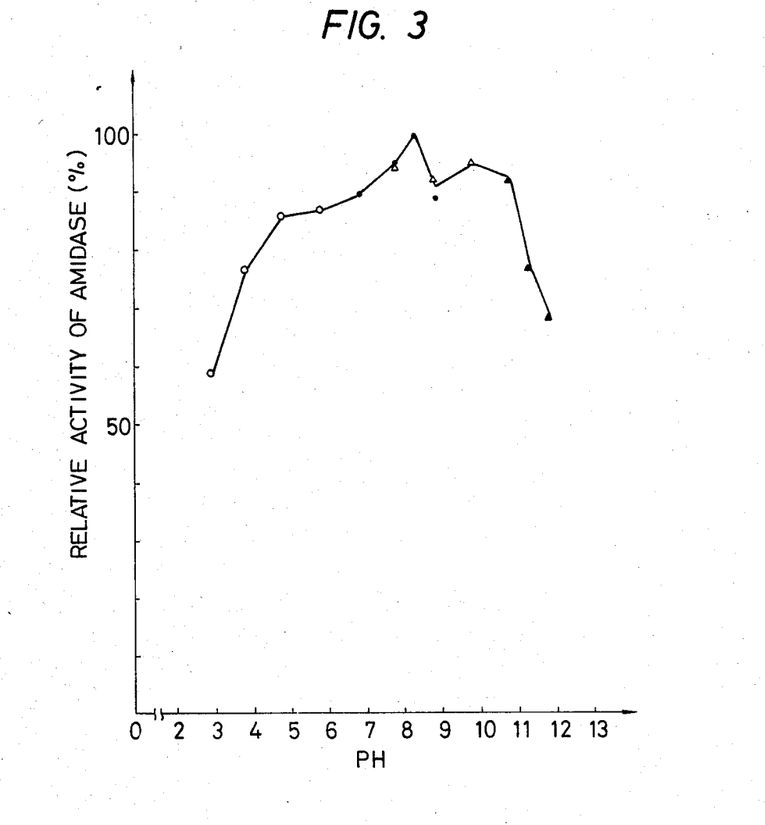

(iv) pH stability: as shown in FIG. 3, the enzyme is stable over a wide pH range of from pH 5.0 to 11.0 at low temperatures (treated at 4° C. for 20 hours).

Figure 4:
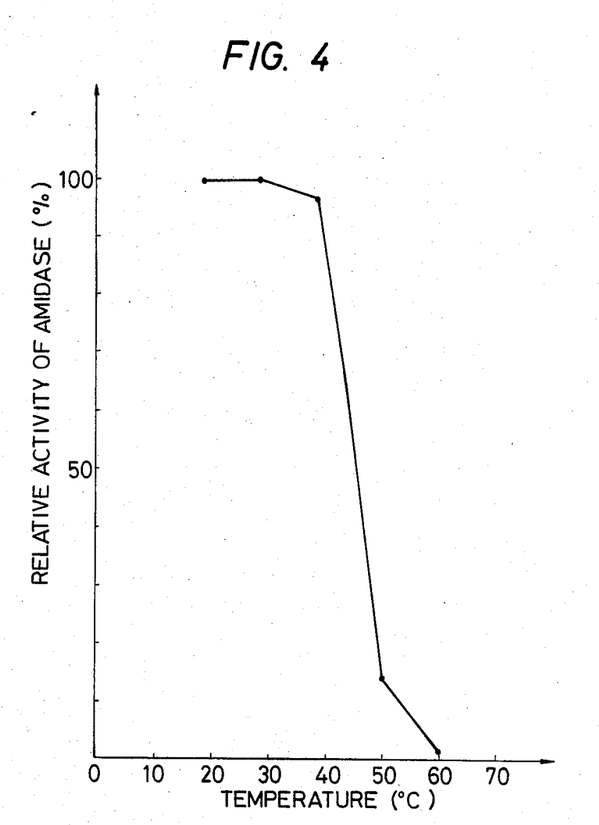
FIG. 4 is a graph showing heat stability.

(v) temperature stability: the enzyme is stable up to 40° C. when heated at pH 9.0 for 15 minutes (refer to FIG. 4).

(vi) substrate reactivity: Amidase activity was measured to Bz-Lys-p-NA, N-benzoyl-L-arginine-p-nitroanilide (hereafter referred to as Bz-Arg-p-NA), L-lysine-p-nitroanilide (hereafter referred to as Lys-p-NA) and L-arginine-p-nitroanilide (hereafter referred to as Arg-p-NA) and esterase activity was measured to TLME and N-tosyl-L-arginine methyl ester (hereafter referred to as TAME) at pH 8 to 9.5 and 30° C. to determine a Michaelis constant (Km) and molecular activity (Kcat) of the enzyme to each of the substrates, and the results shown in Table 1 were obtained. As is clear from Table 1, this enzyme has an extremely high substrate specificity; the amide bond on the carboxyl group of L-lysine or L-arginine was affected in lysine but was not hydrolyzed in arginine. The enzyme hydrolyzed the ester bond of the carboxyl group in lysine or arginine; the action was strong for lysine but extremely weak for arginine.

TABLE 1

| Substrate | Quantitative Analysis* | Reaction pH | KM (mM) | Kcat ($sec^{-1}$) | Kcat/Km |
|---|---|---|---|---|---|
| Bz—Lys—p-NA | A | 9.5 | 0.101 | 1.73 | 17.13 |
| Bz—Arg—p-NA | A | 9.5 | not hydrolyzed | | |
| Lys—p-NA | A | 9.0 | 0.05 | 0.04 | 0.73 |
| Arg—p-NA | A | 9.0 | not hydrolyzed | | |
| TLME | B | 8.0 | 0.09 | 523.1 | 5812 |
| TAME | C | 8.0 | 0.75 | 0.28 | 0.374 |

*Quantitative Analysis
A: Method of Tuppy et al (Z. Physiol. Chem., 329, 278 (1962))
B: Method of Schwert and Takenaka (Biochim. Biophys. Acta, 16, 570 (1955))
C: Method of Masaki et al (Nippon Nogeikagaku Kai, 51, 195 (1977))

(vii) influence of inhibitor and various metal salts: Influences of various inhibitors on amidase activity to Bz-Lys-p-NA are shown in Table 2. Further, influences of various metals ions on amidase activity to Bz-Lys-p-NA are shown in Table 3.

TABLE 2

| Inhibitor | Concentration (mM) | Relative Activity (%) |
|---|---|---|
| No addition (control) | — | 100.0 |
| o-Phenanthroline | 1.0 | 99.3 |
| Enthylenediaminetetraacetate | 1.0 | 99.3 |
| L-Cysteine | 1.0 | 97.8 |
| Monoiodoacetate | 1.0 | 84.4 |
| Diisopropyl phosphofluoride | 1.0 | 70.1 |
| Diisopropyl phosphofluoride | 10.0 | 53.2 |
| Diisopropyl phosphofluoride | 20.0 | 27.5 |
| Phenylethylsulfonyl fluoride | 2.0 | 18.3 |
| p-Chloromercury benzoate | 0.1 | 94.8 |
| Tosyl—L-lysine chloromethyl ketone | 0.1 | 0.0 |
| Tosyl—L-arginine chloromethyl ketone | 0.1 | 79.1 |
| Dithiothreitol | 1.0 | 103.9 |
| Tosyl—L-phenylalanine chloromethyl ketone | 1.0 | 92.2 |

As shown in Table 2, the enzyme is a type of serine protease which undergoes inhibition by diisopropyl phosphofluoride, phenylmethylsulfonyl fluoride and tosyl-L-lysine chloromethyl ketone.

TABLE 3

| Metal Salt | Concentration (mM) | Relative Activity (%) |
|---|---|---|
| No addition (control) | — | 100.0 |
| $ZnCl_2$ | 1.0 | 44.1 |

TABLE 3-continued

| Metal Salt | Concentration (mM) | Relative Activity (%) |
|---|---|---|
| $CaCl_2$ | 1.0 | 102.2 |
| $NaCl_2$ | 1.0 | 99.0 |
| $MnCl_2$ | 1.0 | 101.3 |
| $NiCl_2$ | 1.0 | 83.8 |
| KCl | 1.0 | 90.6 |
| $MgCl_2$ | 1.0 | 95.3 |
| $HgCl_2$ | 0.1 | 109.4 |
| $CoCl_2$ | 1.0 | 98.1 |

As is clear from Table 3, this enzyme is inhibited by zinc ions.

As described above, this enzyme has a property of specifically hydrolyzing the amide bond and the ester bond of the carboxyl group of L-lysine so that it is expected to apply the enzyme to the fields of food chemistry, pharmaceuticals, clinical chemistry, biochemistry, etc., and it can be utilized in such fields.

This enzyme can be used in many forms. The enzyme can be used as it is in the form of a momomer in solution. Alternatively, this enzyme can be cross-linked with a cross linking agent such as glutaraldehyde, diisocyanate, etc. to convert it into a water soluble or water-insoluble protease Ia polymer. This enzyme also can be covalently bound or ionically bound to a water insoluble carrier or enclosed therein to convert the enzyme into a state insoluble in water and to allow the enzyme to be used as an immobilized enzyme. Thus, this enyzme is appropriately and advantageously employed in a mode suited for each utility or purpose.

This novel enzyme has a characteristic substrate specificity that specifically acts on the peptide bond alone at the carboxyl group site of lysine and hydrolyzes the same; for this reason, this enzyme can be utilitzed concretely in enzymatic decomposition of peptides or proteins in the determination of the configuration and order of amino acids and the decomposition and synthesis of lysyl peptides.

As a specific example for utilizing this enyzme, an example of synthesising human insulin from porcine insulin will now be described. The difference between procine insulin and human insulin is that the amino acid at the 30-position is alanine in the former and threonine in the latter. The remaining amino acid configuration is quite common there-between and the amino acid at the 29-position adjacent the 30-position is lysine.

Accordingly, protease Ia and porcine insulin are incubated at pH 8 to 9 to cut the lysyl bond to remove alanine at the 30-position to prepare desalanine insulin (DAI), and DAI is further condensed with threonine or a threonine derivative (for example, threonine butoxide) by this enzyme to convert it to an insulin derivative. It is then possible to convert the thus obtained insulin derivative to human insulin by removing the modifying group in a conventional manner.

Hereafter, the present invention will be explained in more detail with reference to Reference Example and Examples but these Reference Example and Examples are not deemed to limit the present invention.

REFERENCE EXAMPLE 100 ml aliquats of a liquid medium (pH 7.2) containing 1% of peptone, 0.5% of milk casein, 1.0% of saccharose, 0.01% of $K_2HPO_4$ and 0.01% of $MgSO_4.7H_2O$ were separately placed in 500 ml-volume Sakaguchi flasks. After sterilization, the medium was innoculated with *Achromobacter lyticus* M497-1, and incubation was carried out at 28° C. for 24 hours to prepare a good culture liquor. This seed culture liquor, 1.5 l, was transferred to a fermentation tank containing 30 l of the same medium composition, and aeration spinner incubation was carried out for 4 days while feeding 15 l/min of air at 28° C. After cooling 30 l of the thus obtained culture liquor to about 15° C., bacteria were removed using a centrifuge to obtain about 26 l of the supernatant. To the supernatant, 260 ml of a 4% benzalkonium chloride solution was gradually added dropwise while mildly stirring. After allowing to stand at 4° C. for 1 hour, the formed precipitate was removed using a centrifuge to obtain about 25.5 l of the supernatant. To the thus obtained supernatant (4° C.), 80 l of the acetone cooled to −5° C. was gradually added while mildly stirring. After further allowing to stand in the cold overnight, the formed precipitate was collected using a centrifuge and washed with cold acetone to obtain about 40 g of wet precipitate. After drying this wet precipitate with air, the precipitate was dried for 2 days under reduced pressure in a desiccator layed with silica gel to obtain about 14 g of grey white powdery crude enzyme specimen. The amidase activity of the crude enzyme specimen to Bz-Lys-p-NA was 21.6 units/g. In a 10 mM tris-hydrochloride buffer solution (pH 8.0) 10 g of this acetone powder was dissolved and to 500 ml of the resulting crude enzyme solution, 200 g (wet weight) of carboxymethyl cellulose (manufactured by Brown Co., Ltd.) previously equilibrated with a 10 mM tris-hydrochloride buffer solution (pH 8.0) was added. After stirring the mixture mildly for about 1 hour, the mixture was filtered using a glass filter. The ion exchange cellulose on the filter was washed with a suitable amount of the same buffer solution and the washed liquid was combined with the previous filtrate to obtain 725 ml of an enzyme solution. To 725 ml of the obtained enzyme solution, 460 g (wet weight) of diethylaminoethyl cellulose (manufactured by Brown Co., Ltd.) previously equilibrated with the same buffer solution was added. After stirring the mixture at 4° C. for 1 hour, filtration and washing were performed in a manner similar to that described above. The obtained filtrate was condensed using a diaflow membrane UM-10. Thereafter, the condensed filtrate was dialyzed thoroughly to a 2 mM tris-hydrochloride buffer solution (pH 8.0) to obtain 492 ml of an enzyme solution. This enzyme solution was added and adsorbed to a column (4×21 cm) of AH-Sepharose 4B (manufactured by Pharmacia Co., Ltd.) equilibrated with a 2 mM tris-hydrochloride buffer solution (pH 8.0). After thoroughly washing with the same buffer solution, elution was carried out with 2 l of the same buffer solution in which the concentration of sodium chloride was linearly increased from 0 to 1M. The amidase activity portions which eluted at about 0.3M to 0.5M of the sodium chloride concentration were collected. After thoroughly dialyzing this enzyme solution with a 2 mM tris-hydrochloride buffer solution (pH 8.0), the solution was condensed using diaflow membrane UM-10 to obtain 10 ml of a concentrated liquid. This concentrated liquid contained protease I in addition to protease Ia. The amidase activity of this liquid was 14.4 units/ml.

EXAMPLE 1

Figure 5:
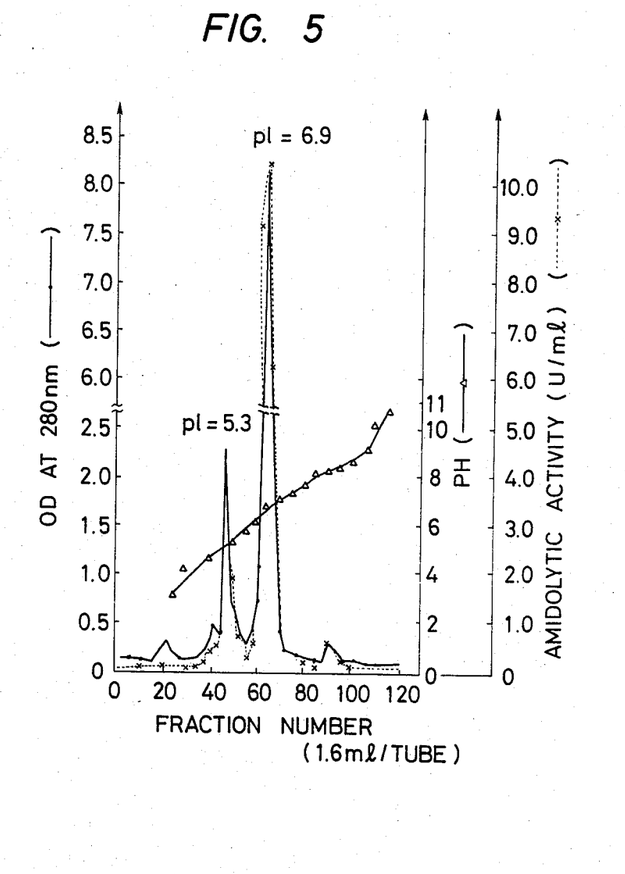
FIG. 5 is a graph showing first focusing electrophoresis-Ampholine (pH 3.5 to 10)

The enzyme liquid, 10 ml, obtained in the Reference Example was placed in a focusing electrophoresis device (inner volume: 150 ml) filled up with Ampholite (manufactured by LKB Co., Ltd.) having pH 3.5 to 10 to carry out isoelectric point fractionation at 4° C. for 48 hours at 600 V. After completion of the electrophoresis, fractionation was carried out by 1.6 ml each to measure the amidase activity of the respective fractions. The results as shown in FIG. 5 were obtained. As is clear from FIG. 5, two peaks of the amidase activity are present. Of these, the latter larger amidase activity peak corresponds to protease I. Among the peaks having the maximum amidase activity at the about 46th fraction of the elution fractions, the former peak of the two activity peaks is not negligible. The desired enzyme is contained in this former peak fraction and 12.6 ml of this fraction was pooled. The amidase activity was 18.9 u, specific activity (u/OD280) was 12.9 and the yield was 8.7% (from acetone powder).

EXAMPLE 2

Figure 6:
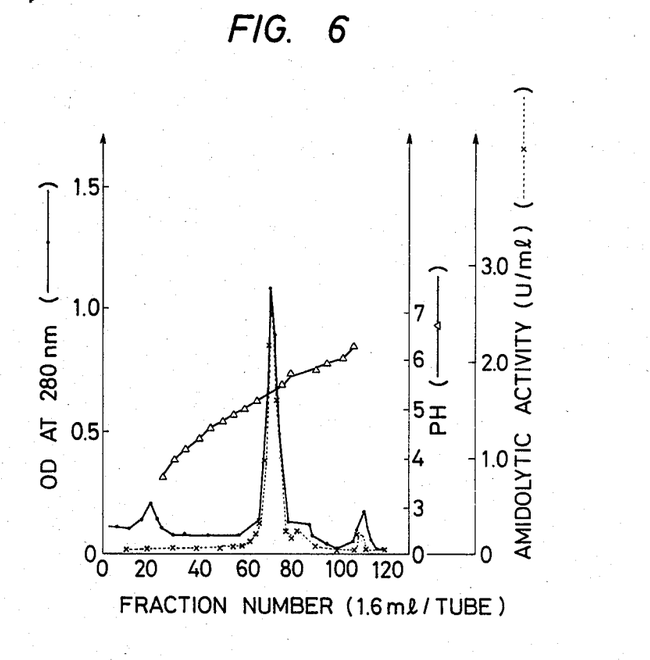
FIG. 6 is a graph showing second focusing electrophoresis-Ampholine (pH 4 to 6).

After dialyzing the enzyme solution obtained in Example 1 with a 2 mM tris-hydrochloride solution (pH 8.0), condensation was carried out. In order to remove impure proteins present still in a trace amount, electrophoresis was repeated using Ampholine (pH 4 to 6) under the same conditions as in Example 1 to obtain the results shown in FIG. 6. Fractions corresponding to Fraction Numbers 65 to 76 were collected. In order to remove Ampholite co-present with this enzyme solution, the enzyme solution was passed through a column (2×50 cm) of Sephadex G-50 equilibrated with a 2 mM tris-hydrochloride buffer solution (pH 8.0). After collecting the amidase activity fractions, the fractions were condensed to obtain 5.4 ml of a purified enzyme solution. The amidase activity was 16.1 units. The specific activity (u/OD280) was 2.24 and the yield was 7.4% (from acetone powder). The thus purified protease Ia of the present invention underwent electrophoresis as a single protein by analysis of a disc electrophoresis method.

This bacteria, *Achromobacter lyticus* M497-1 was deposited in Fermentation Research Institute, Agency of Industrial Science and Technology. The deposition number is the accession number 6718 (FERM P-6718).

While the invention has been described in detail and with reference to specific embodiments thereof, it will be apparent to one skilled in the art that various changes and modifications can be made therein without departing from the spirit and scope thereof.

We claim:

1. A protease having the characteristics described below:
    (i) molecular weight: 30,000 (a gel filtration method using Sephadex G-75);
    (ii) isoelectric point: 5.3;
    (iii) pH reactivity: the optimum pH for its esterase activity is at pH 8.5 and the optimum pH for its amidase activity is at pH 9.0, respectively;
    (iv) substrate reactivity: it selectively and specifically hydrolyzes the ester bond and the amide bond derived from the carboxyl group of L-lysine;
    (v) inhibitor: it is inhibited by diisopropyl phosphofluoride, tosyl-L-lysine chloromethyl ketone and phenylmethylsulfonyl chloride.

2. The protease as claimed in claim 1 wherein said protease is produced by a microorganism belonging to the genus Achromobacter.

3. The protease as claimed in claim 1 wherein said protease is produced by a microorganism belonging to the strain *Achromobacter lyticus.*

4. The protease as claimed in claim 1 wherein said protease is produced by a microorganism belonging to the strain *Achromobacter Lyticus* M497-1 IFO 12725, ATCC 21456, and FERM-P 4420.

5. The protease as claimed in claim 1 wherein said protease is produced by a microorganism belonging to the strain *Achromobacter lyticus* FERM P-6718.

6. A substantially pure protease having the characteristics described below:
    (i) molecular weight: 30,000 (a gel filtration method using Sephadex G-75);
    (ii) isoelectric point: 5.3;
    (iii) pH reactivity: the optimum pH for its esterase activity is at pH 8.5 and the optimum pH for its amidase activity is at pH 9.0, respectively;
    (iv) substrate reactivity: it selectively and specifically hydrolyzes the ester bond and the amide bond derived from the carboxyl group of L-lysine;
    (v) inhibitor: it is inhibited by diisopropyl phosphofluoride, tosyl-L-lysine chloromethyl ketone and phenylmethylsulfonyl chloride.

7. The substantially pure protease as claimed in claim 6, wherein said protease is produced by a microorganism belonging the genus Achromobacter.

8. The substantially pure protease as claimed in claim 6, wherein said protease is produced by a microorganism belonging to the strain *Achromobacter lyticus.*

9. The substantially pure protease as claimed in claim 6, wherein said protease is produced by a microorganism belonging to the strain *Achromobacter Lyticus* M497-1 IFO 12725, ATCC 21456, and FERM-P 4420.

10. The substantially pure protease as claimed in claim 6, wherein said protease is produced by a microorganism belonging to the strain *Achromobacter lyticus* FERM P-6718.

* * * * *